United States Patent [19]

Donahoe et al.

[11] Patent Number: 4,487,833
[45] Date of Patent: Dec. 11, 1984

[54] METHOD OF PREPARING HYBRIDOMAS AND OF PURIFYING IMMUNOGENIC MATERIALS

[75] Inventors: Patricia K. Donahoe, Weston; Gerald P. Budzik, Waltham; Meredith Mudgett-Hunter, Hyde Park, all of Mass.

[73] Assignee: The General Hospital Corporation, Boston, Mass.

[21] Appl. No.: 353,089

[22] Filed: Mar. 1, 1982

[51] Int. Cl.$^3$ .................... C12N 15/00; C12N 5/00; C12N 5/02; C12P 21/00; G01N 35/54
[52] U.S. Cl. ................................. 435/172.2; 435/240; 435/241; 435/68; 436/548; 935/90; 935/95; 935/104
[58] Field of Search ................. 435/172, 240, 241, 68, 435/172.2; 436/548

[56] References Cited

U.S. PATENT DOCUMENTS 4,172,124 10/1979 Koprowski et al. ................. 424/85
4,196,265 4/1980 Koprowski et al. ................. 435/2
4,271,145 6/1981 Wands et al. ....................... 424/85

OTHER PUBLICATIONS

Budzik et al.: Cell 21, 909 (1980).
Springer: J. Biolo. Chem. 256, 3833 (1981).
Mudgett-Hunter et al.: Fed. Proc. 40, (3 part II), p. 995, Abstract No. 4338 (1981).
Picard et al.: Chem. Abstr. 90, 50003g (1979) of Mol. Cell. Endocrinol. 12, 17 (1978).
Milstein: Scientific American, Oct. 1980, pp. 66–74.
Goding: J. Immunolog. Meth. 39, 285 (1980).
Rosenwaks, *Journal of Clinical Endocrinology and Metabolism*, 52:817 (1981).

Rosenwaks et al., Abstract 174, 65th Annual Meeting, *Program and Abstracts*, Jun. 8, 1983.
Fuller et al., *Gynecologic Oncology*, "Mullerian Inhibiting Substance Inhibition of a Human Endometrial Carcinoma Cell Line Xenografted in Nude Mice," 1984 (preprint).
Mudgett-Hunter, M. et al., "Monoclonal Antibody to Mullerian Inhibiting Substance", 1981 FASEB Abstract Form, Immunology.
Vigier, B. et al., Endocrinology, vol. 110, pp. 131–137 (1982).
Secher, Nature, vol. 285, pp. 446–450 (Jun. 1980).

*Primary Examiner*—Thomas G. Wiseman
*Assistant Examiner*—James Martinell
*Attorney, Agent, or Firm*—Saidman, Sterne, Kessler & Goldstein

[57] ABSTRACT

In a method for preparing a monoclonal hybridoma which secretes antibodies against an immunogenic material, comprising sensitizing an appropriate source with an immunizing amount of a preparation of the immunogenic material, obtaining from the source lymphocytes having immune activity against the immunogenic material, and fusing the lymphocytes with an appropriate cell line to thereby form mixed hybridomas, the improvement wherein: the immunogenic material is present in the immunizing preparation in an amount not larger than 5% by weight, and wherein, after formation of the mixed hybridomas but prior to cloning, the method comprises the steps of: raising ascites fluid with the mixed hybridomas, then detecting immune specificity against the immunogenic material in the ascites raised fluid; and thereafter cloning the ascites raised cells which show immune specificity against the material.

21 Claims, 5 Drawing Figures

SELECTION OF
MONOCLONAL ANTI-MIS ANTIBODIES

1. IMMUNIZE

2. CELL FUSION

3. RIA SELECTION OF MIXED HYBRIDOMAS

4. ASCITES PRODUCTION ←─────────────────┐

5. SPECIFICITY TEST:                    │
      ANTI-MIS AFFINITY ADSORPTION       │
     ╱          ╲         │
  PBS FALL-THRU      NH$_4$ SCN ELUTED │
    |─── ORGAN CULTURE ───|         │
    ↓      ASSAY     ↓         │
  NEGATIVE           POSITIVE      │

6. SUBCLONE MIXED HYBRIDOMAS            │
    WHICH ADSORB MIS ACTIVITY           │

7. RIA SELECTION OF MONOCLONAL HYBRIDOMAS ┘

FIG. 2

METHOD OF PREPARING HYBRIDOMAS AND OF PURIFYING IMMUNOGENIC MATERIALS

BACKGROUND OF THE INVENTION

This work was supported by National Cancer Institute, Grant No. CA17393.

FIELD OF THE INVENTION

The present invention relates to processes for preparation of hybridomas and of purification of biological materials, especially the purification of Mullerian Inhibiting Substance (MIS).

BRIEF DESCRIPTION OF THE PRIOR ART

The efficient and rapid purification of biological materials such as proteins, nucleic acids or polysaccharides, has been of great interest and has received great attention in the last few years. The use of immunoaffinity chromatography has been considered a prime candidate for research and development, because of the theoretical advantages inherent in the method.

For example, a given protein X brought to high purity by laborious classical purification methods, can be used as an antigen to immunize test animals to produce specific anti-X antibodies. A sample of the protein is immobilized to obtain a selected adsorbent which is used to isolate anti-X from the hyperimmune animal serum. The highly purified antibody so obtained is in turn immobilized. The second adsorbent comprised of anti-X ligands can now be used to harvest protein X from its crude source, possibly in a single step. This complex way of obtaining the selected immunoadsorbent is generally justified by the simplification achieved for the isolation of more protein X, as well as by its reusability in any repeat isolations of the ligate. The repetitive use of immunoadsorbent chromatography may reduce labor significantly. (See, for example, Nishikawa, "Affinity Chromatography," pages 35-54, in Kirk-Othmer, *Encyclopedia of Chemical Technology*, 3d ed., (1979), at page 38).

The use of monoclonal antibodies for large-scale purification of substances present in a crude biological preparation has also quite recently received attention (see, for example, Secher and Burke, Nature, Vol. 285, June 1980, pp. 446-450.) Thus, a clone of hybrid myeloma secreting a mouse monoclonal antibody to human leukocyte interferon has been isolated by these authors. The antibody neutralized the antivirulent activity of the interferon and, when attached to a solid support and used as an immunoadsorbent, allowed interferon purification of up to 5,000-fold in a single step. It appears from the work of Secher and Burke that the use of monoclonal antibodies is ideal in cases where the desired substance is to be purified from a biological mixture wherein it is present in very low concentrations (for example about 1% by weight of protein).

In particular, it would be highly desirable to develop a process wherein any biological material present in low amounts in a mixture can be purified by immunoadsorbent chromatography, using a monoclonal antibody, but wherein the material is not a priori available in substantially purified form. If the material is available in substantially purified form, such as in the case of the Secher and Burke interferon, then immunization with a purified antigen is expected to produce a much narrower population of antibody-producing lymphocytes and thus of hybridomas. Furthermore, and most importantly, availability of a substantially purified antigenic material is crucial in order to select the desired hybridoma cells prior to subcloning, as is standard in the art and as was, in fact, done by Secher and Burke.

The more common case, however, is that wherein the material to be isolated and purified from the mixture is not a priori available in substantially purified form and all one has to work with is a crude mixture. It would be desirable, therefore, to develop techniques that can solve this problem. Such techniques are described in the present application.

One protein which has received particular attention recently and for which a rapid and efficient purification system would be desirable is Mullerian Inhibiting Substance (MIS). MIS is a substance with the properties of inducing regression in the Mullerian duct, the fetal analog of the uterus, fallopian tube and vagina. Donahoe et al, J. Surg. Res., 23:141-148 (1977), demonstrated that a high level of MIS persists in newborn calf testes for up to 8 weeks after birth. This tissue has provided a ready source for the partial purification and characterization of the biologically active moiety, by guanidine hydrochloride extraction (see, for example, Swann, D. A. et al, Developmental Biology, 69:73-84 (1979); Donahoe et al, Pediatric Andrology, 37-46, (1981), Martinez Nijhoff Pub., The Hague, Boston/London; Donahoe et al, Science, 205:913-915 (1979)).

Purification of MIS from calf testes has been a tedious undertaking, since large quantities of material are consumed in the assay required for activity confirmation. In spite of these problems, interest in MIS purification remains high, since impure fractions with MIS activity are slightly toxic to human ovarian cancer in vitro (Donahoe, P. K., Science, 205:913-915 (1979)).

Incubation of fetal calf testes in media for four hours show that MIS can also be secreted (Josso, N. et al, Biol. Reprod., 13:163-167 (1975)). Homogenization of testes tissue, however, has not yielded active preparations (Donahoe, P. K. et al, Cryobiol., 14:534-542 (1977); Josso, N. et al, Recent Prog. Hormone Res., 33:117-167 (1977)). U.S. patent application Ser. No. 303,516, filed Sep. 18, 1981, which is a continuation of Ser. No. 071,316, filed on Aug. 30, 1979 to Patricia K. Donahoe et al for "Purified Mullerian Inhibiting Substance and Process for Treating Human Ovarian Cancer Cells," describes a process for purifying MIS from testes by using aqueous polar dissociative solutions, separation of DNA and RNA, fractionation by gel filtration chromatography, elution, and isolation of the MIS. U.S. patent application 287,943, filed July 29, 1981, now U.S. Pat. No. 4,404,188 to Patricia K. Donahoe et al, entitled "Purified Mullerian Inhibiting Substance and Method of Purification" describes a process for purifying MIS which comprises treatment with a protein inhibitor, chromatography on ion exchange, chromatography on wheat germ lectin, on concanavalin A and/or on a supported triazinyl dye. Both of these patent applications are herein incorporated by reference. Neither of these applications or of the aforementioned prior art, however, use immunoaffinity chromatography for the isolation and purification of MIS.

A need, therefore, continues to exist for the development of a highly efficient technique for immunoaffinity chromatography using monoclonal antibodies, wherein a biological substance can be isolated from a complex biological mixture without the availability, a priori, of said biological substance in question in substantially purified and/or homogeneous form.

In particular, the need exists for an immunoaffinity chromatography method as hereinbefore, for the isolation and purification of MIS from animal testes.

SUMMARY OF THE INVENTION

It is therefore an object of the invention to provide a method of immunoaffinity chromatography for biological materials using monoclonal antibodies It is another object of the invention to provide a method for preparing hybridomas, and monoclonal antibodies against an immunogenic material which is present in a biological mixture in extremely low amounts It is another object of the invention to provide a method for the purification of MIS.

It is yet another object of the invention to provide hybridoma cell lines and monoclonal antibodies derived therefrom, which antibodies have specificity against MIS.

These and other objects of the invention have been obtained by providing:

In a method for preparing a monoclonal hybridoma which secretes antibodies against an immunogenic material, comprising sensitizing an appropriate source with an immunizing preparation of said immunogenic material, obtaining from said source lymphocytes having immune activity against said immunogenic material, and fusing said lymphocytes with an appropriate cell line to thereby form mixed hybridomas, the improvement wherein:

said immunogenic material is present in said immunizing preparation in an amount not larger than 5% and wherein after formation of said mixed hybridomas, the method comprises the steps of:

raising ascites fluid with said mixed hybridomas; then detecting immune specificity against said immunogenic material in said ascites raised fluid; and then cloning the ascites-raised cells which show immune specificity against said material.

Another object of the invention has been obtained by utilizing the monoclonal antibodies derived from the cells obtained in the aforesaid method in a process for purifying said immunogenic material from said immunizing preparations.

Another object of the invention has been obtained by providing monoclonal antibodies derived from cells prepared as hereinabove having specificity against Mullerian Inhibiting Substance from testes.

Yet another object of the invention has been obtained by providing a method of purifying MIS from testes by utilizing monoclonal anti-MIS prepared in the aforesaid manner. DESCRIPTION OF THE DRAWINGS The aforementioned invention will be better understood by reference to the following description when taken together with the attached drawings, wherein:

FIG. 2 shows an experimental protocol for raising and selecting hybridoma cell lines which secrete monoclonal antibodies specific for MIS.

Figure 3:
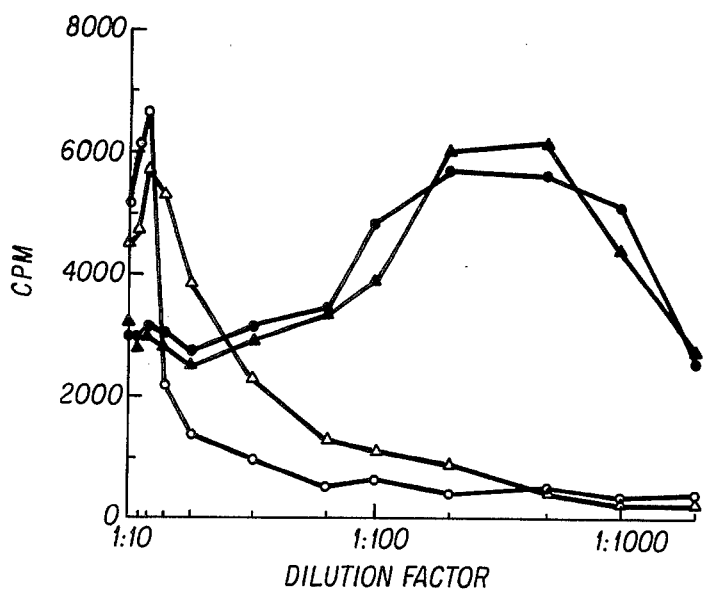

FIG. 3 shows the titration of culture media and ascites fluid obtained from two subcloned cell lines from mixed hybridoma IDI by the solid phase PVC plate radioimmunoassay. The culture media is shown in open symbols: IB2 (—▲—) and IIB6(—●—). Ascites is shown in closed symbols: IB2 (— —) and IIB6 (— —).

Figure 4:
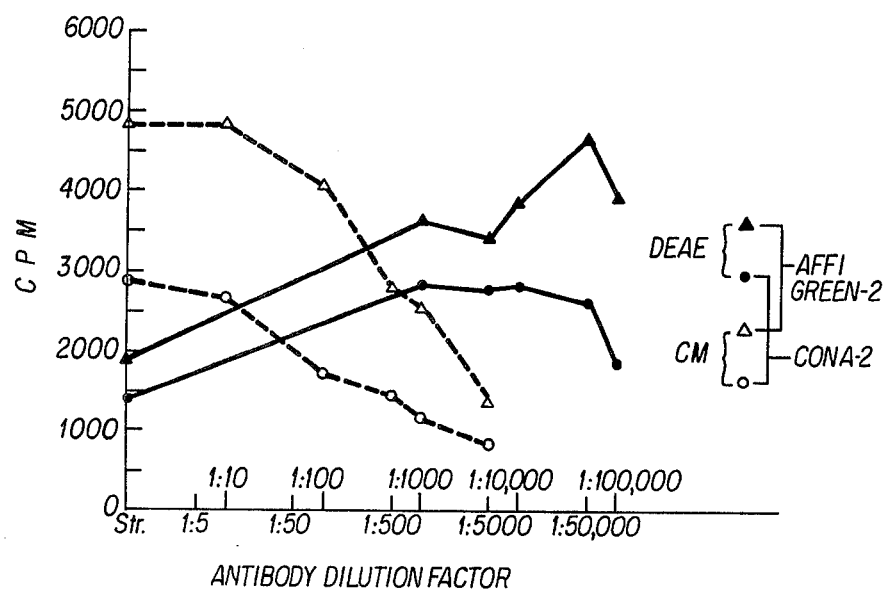

FIG. 4 shows the titration of monoclonal antibody IIIB3 using two different MIS preparations by the solid phase PVC plate RIA. IIIB3 culture media shown in symbols, on Con A-2 MIS (—o——o—) and on Affi Green-2 MIS (—△—). IIIB3 IgG prepared from ascites fluid by DEAE chromotography shown in closed symbols, on ConA-2 MIS (—●—) and on Affi Green-2 MIS (—▲—).

Figure 5:
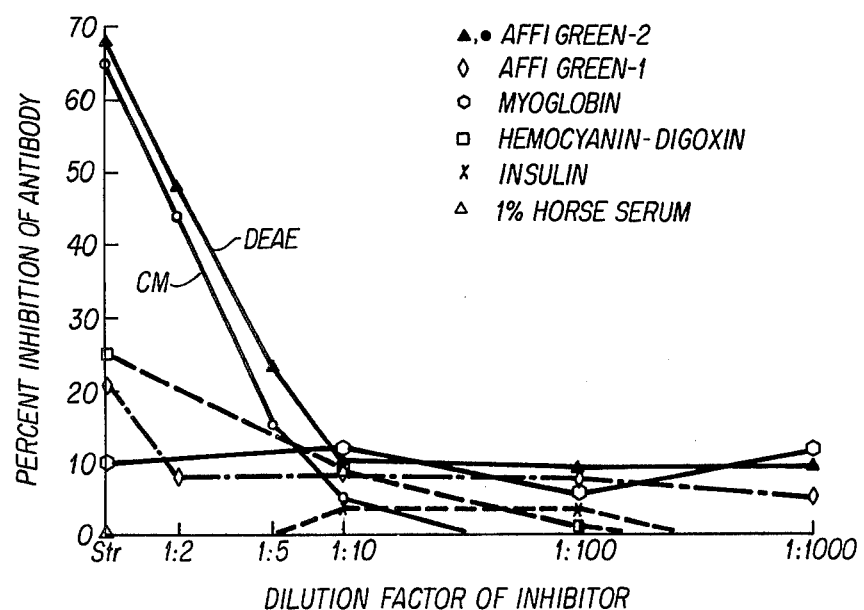

FIG. 5 shows the inhibition of binding of monoclonal anti-MIS antibody present in culture media to MIS prep Con A-2 (7,000-fold purified), in the solid phase PVC plate radioimmunoassay by various protein solutions: 1% horse serum (—+—), insulin (—×—), hemocyanin-P coupled to digoxin (—□—), myoglobin (—◯—), and Affi Green-1 (—◇—). Homozygous inhibition curves with MIS preparation Green-2 (15,000-fold purified MIS) are shown for anti-MIS antibody IIIB3 present in culture media (CM) (—●—) and in an IgG preparation (DEAE) from ascites fluid (—▲—).

DESCRIPTION OF THE PREFERRED EMBODIMENTS

The present invention is based on the discovery of an unusual step in the otherwise common method of preparing monoclonal antibodies Because most biological substances, such as proteins, polysaccharides or nucleic acids, are present in the immunizing antigenic material in amounts normally about or less than 1% by total weight, and because these substances have not independently been purified to homogeneity, it is normally not possible to follow the standard technique for preparing monoclonal antibodies with the same ease. The problem is that since no homogeneous antigen exists, it is difficult, if not impossible, to select monoclonal lines specific for the antigen from the initial mixed hybridomas. Any immunoassay which is used to select for the monoclonal lines cannot discriminate among antibodies specific for the immunogenic material and for the impurities. Many times, the immunogenic material can only be demonstrated by affecting biological activity in complicated culture assays Since many of these culture assays require milligram quantities of protein, it is necessary to have comparable amounts of antibody These problems were solved in the present invention by taking the unusual step of raising ascites fluid with mixed hybridoma cell populations prior to subcloning. Only those mixed hybridoma cell populations which after ascites raising demonstrate appropriate specificity for the biological material in question, are subsequently cloned.

In other words, in the present invention ascites fluid is raised prior to subcloning, in contrast to the prior art where ascites fluid is raised after subcloning. It could not be expected beforehand that such a system would work, and the present invention demonstrates that even un-subcloned hybridoma mixtures may be used to raise ascites with preservation of specific antibody production. If this step is omitted, ascites from many subclones would have to be screened, in order to determine which has the requisite specificity for the biological material in question. The power of this technique is such that it may very well be the only method for purifying any biological substance present in a mixture in a level of less than about 1% by weight, by immunoaffinity chromatography.

Figure 1:
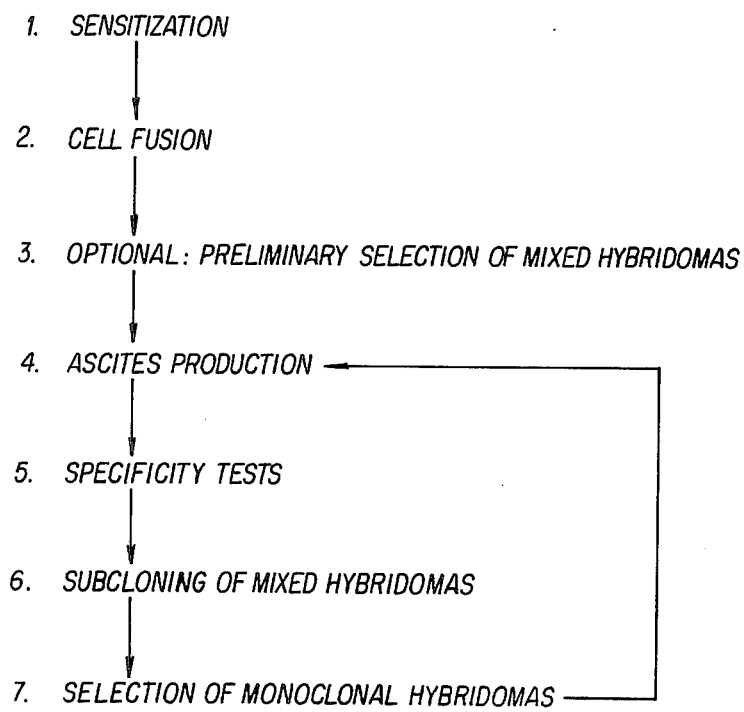
FIG. 1 shows a general protocol for raising and selecting hybridoma cell lines which secrete monoclonal antibodies specific for any immunogenic substance present in an immunizing preparation in low amounts by weight.

The present invention can be readily understood by reference to FIG. 1 which shows a generalized protocol for the selection of monoclonal antibody, using the steps of the invention. After sensitization, cell fusion, and optional preliminary selection of mixed hybridomas, the mixed hybridomas are injected into an animal for the production of ascites. The ascites is then tested for specificity, and the mixed hybridomas obtained therefrom are subcloned, and selected for specific monoclonal hybridomas. The monoclonal hybridomas can then be used to induce further ascites, as in the prior art.

The general techniques of sensitization and/or immunization, cell fusion, ascites production, selection of mixed hybridomas, of subcloning of monoclonal hybridomas are generally well known in the art. Attention, for example, is brought to Koprowski et al, U.S. Pat. No. 4,172,124, Koprowski et al, U.S. Pat. No. 4,196,265, Wands et al, U.S. Pat. No. 4,271,145, or Douillard, J. Y. and Hoffman, T.: "Basic Facts About Hybridomas," in Compendium of Immunology, Vol. II, L. Schwartz, ed. (1981), which are herein incorporated by reference.

Generally, the first stage is the generation of lymphocytes suitable for fusion. In the case of soluble immunogens in a mixture, hyperimmunization is usually required (see, for example, Stahli, C. et al, J. Immunol. Meth., 32:297 (1980)). The immunization schedule usually entails two to three injections at intervals of up to a few weeks, with the last injection three to four days before the fusion. Adjuvants have sometimes been used, especially when using soluble antigens such as are preferred in the present case. In vitro sensitization is also advantageous, especially in the present case where only small amounts of antigen are available, or where the immunogen might be potentially noxious to the host.

By "sensitization of a source" is meant immunization of an animal or of an in vitro cell line. It will normally occur with an impure substance which is present in a complex biological mixture in amounts of generally less than 5%, normally less than 3%, or preferably less than 1% by weight of the mixture. The material may be a peptide or a protein (such as an enzyme, a hormone, an antibody, a glycoprotein, or a receptor); it may be nucleic acid; or it may be a polysaccharide, such as, for example, a lipopolysaccharide. If the immunogen is of small molecular weight, the whole mixture is coupled to a carrier such as BSA. The impurifying material may be one or more of the aforementioned mixtures and will normally consist of a cell extract containing varying amounts of nucleic acid, protein, lipids and saccharides. A preliminary purification of the material is, of course, possible but not necessary. Such purification may be carried out by standard means, such as ion exchange chromatography, precipitation, isoelectric focusing and the like. The only important thing is that the material be immunogenic, i.e., capable of raising antibodies in the lymphocyte source.

The cell lines suitable for fusion should show rapid uniform growth characteristics, deficiency of metabolism for one or more component of the hybridoma growth medium, (or any other distinguishing characteristics over the final hybridomas), and potential for good fusion frequency. The immortalizing line is generally derived from the same species as the lymphocytes, since intra-species hybrids work better than inter-species hybrids. Several plasmacytoma derived lines are available, including mutants selected for loss of ability to secrete myeloma immunoglobulin. For example: MPC11-X45-6TG or "X45", (a Balb/c plasmacytoma); P3-NS1-1-Ag4-1 or "NS1" (Kohler, G. et al, Euro. J. of Immunol., 6:292 (1976)); P3-X63-A68 or "X63" one of the original lines, is a $MOPC_{21}$ variant and secretes IgG (k). Recent mutants of this line have been developed which no longer secrete immunoglobulins but still may be fused with somatic cells (see, for example, Kearney, J. F. et al, J. Immunol., 123:154 (1979)); sp2/0-Ag14, is another Balb/C myeloma line (Shulman, N. et al, Nature, 276:269 (1978). Of course, any suitable immortalizing line, whether from rats, mice, or humans or any other source can be used.

Fusion of the lymphocytes derived from sensitization with the immortalizing line, can be carried out by viruses (see, for example, Harris, H. et al, Nature, 205:640 (1965)), polyethylene glycol (PEG) (see, for example, Bontecorvo, G., Som. Cell Genetics, 1:397 (1975)) or any other fusion-inducing agent. For example, several examples of PEG have been used having molecular weights ranging from 1,000 to 6,000. PEG is normally used diluted with 30%-50% saline or serum-free medium. Exposure to PEG for 1-2 minutes appears to be optimum to prevent toxicity to the cells; temperatures of about 37° are recommended. Myeloma/spleen cell ratios are recommended between 2:1 to 1:10.

Once fusion has occured the mixture of cells contains hybrids, fused and unfused spleen cells, and malignant cells. Spleen cells cannot generally maintain growth in routine culture medium and will eventually die out. Malignant cells would keep on dividing and overgrow the hybrids unless a selective medium is used that will allow only the growth of hybrids, or unless malignant cells are used which can be distinguished from the hybrids by any other technique. The malignant lines chosen for fusion are often hypoxanthine-guanine phosphoribosyl transferase (HGPRT) deficient, which will not grow in aminopterine-containing medium because of their inability to synthesize purines from thymidine and hypoxanthine. The selection medium is normally composed of hypoxanthine $1 \times 10^{-4}$ M, aminopterine $4 \times 10^{-7}$ M, and thymidine $1.6 \times 10^{-5}$ M, commonly called HAT medium (see Littlefield, J. W., Exp. Cell Res. 41:190 (1966)). The feeding schedules for the fused cells usually require feeding of HAT medium on days 1, 7 and 10 and then growth in either regular culture medium or hypoxanthine, thymidine containing medium. Any maintenance medium which is useful for the growth of hybrids, such as standard tissue culture medium can then be used.

After selective growth of the hybrids, the prior art has normally screened cells from the mixed hybridomas by radioimmunoassays or enzyme linked immunoassays, wherein the antigen is bound to a solid support and allowed to react with hybridoma supernatants containing antibodies. This requires substantially purified immunogen bound to a solid phase, so that such solid phase radioimmunoassay techniques can be utilized. On the other hand, in the present invention, the immunogen is not present in substantially purified form a prior, and therefore cannot be used to effectively screen the population of mixed hybridomas. In the present invention then, the next step is the raising of ascites fluid with the population of mixed hybridomas. Raising ascites from a mixed hybridoma cell population is necessary in cases where antibody must be obtained in sufficient quantity (mg) to assist in biological specificity determinations prior to subcloning.

It is normally useful to carry out a preliminary, rough screening of the mixed hybridomas, in order to gain some assurance that the ascites raising will be carried out against a fraction containing antibodies against the immunogen present in the original impure biological mixture. This is preferred since the mixed hybridoma population contains a very large fraction of cells which secrete antibodies against antigens or immunogens originally present in the source, i.e., most usually, present in the original animal. By a rough determination prior to raising ascites fluid, it is commonly possible to eliminate a large fraction of undesired cells. After such screening, the next step is ascites fluid raising.

Thus, mixed hybrids are transferred into animals with inflammatory ascites. Ascites may be induced by peritoneal injection of mineral oil or 2, 6, 10, 14 tetramethylpentadecane (pristane), 10–16 days in advance. Under these conditions antibody containing ascites can be harvested 8–12 days after IP injection of $10 \times 10^7$ cells. Ascites contain higher concentration of antibodies, but includes both monoclonal antibodies and immunoglobulin from the inflammatory ascites. Similar considerations obtain for the serum of animals bearing ascites. Normally, growth of interspecies hybrids in animals implies that immunosuppression of the host has to be carried out, by total body irradiation and administration of antilymphocyte serum prior to injection. Athymic nude mice can also be chosen as the immunodepressed host.

After collection of the ascitic fluid, the technique of the present invention requires the standard specificity and selection tests normally used in the prior art in order to find the antibodies specific for the desired immunogen in question. The specificity tests can, however, now be carried out in larger amounts (normally mg) of antibodies in the supernatants. Standard techniques such as radioimmunoassay or enzyme immunoassays are used.

After selection for a specific desired hybridoma, the heterogeneous colony has to be cloned in order to get a homogenous line expressing a given function. Cloning of hybrids is usually performed after 5–16 days of cell growth in selected medium. Later cloning of hybrids is not preferred. Cloning can be performed by the limiting dilution method in fluid phase, or by directly selecting single cells growing in semisolid agarose. In limiting dilution, cell suspensions are diluted serially to yield the statistical probability of having only one cell per well. In agarose, hybrids are seeded in a semisolid upper layer over a lower layer containing feeder cells. The colonies from the upper layer may be picked up and eventually transferred to wells.

Antibody-secreting hybrids which have been selected can be grown in various tissue culture flasks, and yield supernatants with variable concentrations of desired antibodies in the range of 10–100 micrograms per ml. In addition, for higher concentrations, the desired hybrids can again be transferred into animals with inflammatory ascites.

Once the monoclonal hybridoma has been prepared, it is a matter of routine in the art to isolate the desired antibodies from the supernatant. Well known techniques, such as salt precipitation, gel chromatography, ion exchange chromatography, affinity chromatography, and the like can be used to obtain the antibodies in substantially pure form. By "substantially pure form" it is meant that the antibodies are essentially free from non-monoclonal antibody impurities, such as other proteins, other antibodies having different specificity, nucleic acids, polysaccharides, cell fragments, and the like. The antibodies can be used in soluble form or can be immobilized on an aqueous insoluble solid phase, to obtain insolubilized antibodies.

The antibodies produced by a method of the present invention can be utilized in any of the myriad of applications normally described for such antibodies. For example, they can be used in the development of a radioimmunoassay or enzyme linked immunoassay for the immunogen in question. They can most preferably be used as immunoaffinity ligands for the purification of the immunogen in question. They can also be used in therapeutic processes, in linkage to drugs, and the like.

In a preferred embodiment of the present invention, the immunogen being purified and isolated from a biological mixture containing the same is Mullerian Inhibiting Substance (MIS). Preferably partially purified fractions of MIS are utilized as the immunogenic material. For example a 30-fold pure or a 7,000-fold fraction can be used, (Budzik, G, et al, Cell 10:909 (1980), which is herein incorporated by reference). Significant titers of antibodies to MIS are obtained in serum from mice immunized with such crude MIS preparations. Spleen cells from these mice can be fused, for example, with the NSI myeloma line.

The procedure for selecting monoclonal lines specific for MIS is outlined in FIG. 2. This protocol is the one of the present invention and is followed because the MIS antigen preparation used to coat the radioimmunoassay plates contain other contaminating proteins in addition to MIS. Thus such radioimmunoassay does not discriminate among antibodies specific for MIS which can at the present, only be demonstrated by affecting biological activity in an organ culture assay. The bioassay, however, requires milligram quantities of protein and hence, a comparable amount of antibody to block MIS activity. In order to obtain anti-MIS antibody in sufficient quantities for the bioassay, it is necessary to raise ascites fluid from hybridoma cell populations prior to subcloning. Only the mixed hybridoma cell populations whose ascites demonstrate appropriate specificity for MIS by virtue of their ability to remove biological activity are subsequently cloned. In order to augment the anti-MIS antibody production, mixed hybridoma cell populations are injected into pristane primed mice for ascites fluid production. After selection of the appropriate mixed hybridoma lines these are then subcloned by limiting cell dilution, for example on a feeder layer, and the cell line which tests positive in the radioimmunoassay is isolated.

Therefore, although an impure fraction of MIS is used to immunize mice, somatic cell fusion of immune spleen cells yield monoclonal hybridoma cell lines secreting antibodies specific for MIS. Specificity of the antibody is demonstrated by its ability (1) to adsorb biologically active MIS prior to an organ culture assay and (2) to compete favorably with other potentially cross reacting preparations in a solid phase radioimmunoassay.

The power of the somatic cell fusion technique is realized two-fold. First, in spite of the impurities present in the MIS preparation used for immunization and the preliminary screening radioimmunoassay, a monoclonal antibody specific for MIS is obtained. Second, the invention demonstrates that even unsubcloned hybridoma mixtures may be used to raise ascites with preservation of specific antibody production. If this step is omitted, ascites for many subclones would have to be screened by the bioassay in order to determine which has the requisite specificity for MIS.

Monoclonal antibodies against MIS can be used in a variety of ways. For example, they can be used for the further purification of MIS by a "one-step" immunoaffinity chromatography system; they can be used in studies designed to determine the tissue localization and distribution of MIS; they can be utilized in the establishment of a radioimmunoassay or enzyme linked immunoassay system for MIS; and the like.

Having now generally described this invention, the same will become more readily understood by reference to a specific example which is included herein for purposes of illustration only and is not intended to be limiting unless otherwise specified.

EXAMPLE

MONOCLONAL ANTIBODY TO MULLERIAN INHIBITING SUBSTANCE.

Methods and Materials

Purification of Mullerian Inhibiting Substance:

Fractions of MIS enriched 7,000-fold were obtained as follows. Briefly, newborn calf testes were dissected, rapidly chopped and subsequently incubated at 37° C. for 45 min. Benzamidine (Sigma) was added to a 5 mM final concentration and the suspension centrifuged overnight. The supernatant was decanted, concentrated and rapidly passed through Sephadex ® G-25 for re-equilibration into 10 mM sodium phosphate (pH 8.0), 0.05 M NaCl. This and all other subsequent procedures were performed at 4° C. This fraction was put through DEAE Bio-Gel A and the unbound MIS fraction collected. The pH was adjusted to 6.0 and the material loaded on CM Bio-Gel A through which the MIS also passed unretarded Without further equilibration, this fraction was loaded on wheat germ lectin-Sepharose 6MB (Pharmacia), the column washed with phosphate buffered saline (PBS), and the MIS activity eluted with N-acetylglucosamine. This MIS fraction was similarly loaded on concanavalin A-Sepharose 4B and the 7,000-fold purified MIS fraction eluted with 1-0 methyl- α-D-glucopyranoside.

Fractions enriched 15,000-fold were obtained following dye affinity chromatography. The bound MIS fraction from the wheat germ lectin column was concentrated and dialyzed against 10 mM sodium phosphate (pH 8.0), 0.15 M NaCl and 5 mM 2-mercaptoethanol. This material was loaded on a 2 ml column of Matrex Gel Green A ® (Amicon Corp.), equilibrated with the same buffer. The column was washed with approximately 10 volumes of the starting buffer to remove unbound proteins. The bound fraction containing the MIS biological activity was subsequently eluted with 10 volumes of 10 mM sodium phosphate (pH 8.0), 1.0 M NaCl, 5 mM 2-mercaptoethanol. The column was regenerated following each use with 5 M guanidine-HCl and stored in PBSA.

During the early stages of purification, biologically active fractions were achieved after 1 M guanidine-HCl extraction followed by density gradient sedimentation, gel filtration, and ion exchange chromatography to achieve a 200-fold purification. This method, using a dissociation solvent, was followed to assure that the biological activity was associated with a macromolecular constituent. The preparation was used in the earliest screening RIA described below. Once this presumption was confirmed, the purification procedure from incubation media was used exclusively.

All chromatography fractions were concentrated by ultrafiltration and dialyzed against PBS at 4° C. for at least 24 hr. before bioassay via the organ culture of Donahoe et al (J. Surg. Res., 23:141 (1977)).

Organ Culture Assay: A graded organ culture assay for the detection of MIS was carried out. Test samples (0.35 ml) were added to media of the organ culture dishes and incubated for 72 hours after which tissues were fixed, stained, and the histologic sections analyzed for Mullerian duct regression which was graded using morphological criteria on a scale of 0 (no regression) to 5 (complete regression) using the 14½ day urogenital ridge of the female rat embryo.

Immunization: Balb/C mice (Jackson Labs) were injected i.p. with 0.2 mg of crude MIS preparation (30-fold purification Dev. Biol., 69:73 (1979) or 7,000-fold purification (Cell, 10:909 (1980)), in 0.2 ml of a 1:1 suspension with complete Freund's adjuvant. The same dose was repeated i.p. 1 month and 2 months later. Three days prior to fusion, mice were given an I.V. boost at 1/10 the concentration of the initial injection of the crude MIS preparation in saline (0.2 ml).

Media and Cell Lines: The HAT-sensitive myeloma cell line, P3-NS1/1Ag4-1 (NS1) (*Eur. J. Immunol.*, 6:292 (1976)) was used. Cultures were maintained in high glucose Dulbecco's Modified Eagle's Medium (DMEM) supplemented with 20% fetal calf serum (FCS), 50 µg/ml gentamicin, and 580 µg/ml glutamine. Hybrids were selected in HAT medium (Science, 145:709 (1964)) cultured in HT media (HAT minus aminopterin) for several generations.

Cell Fusion: Spleen cells from immunized mice were fused with the myeloma lines NS1 as described by Marshak-Rothstein et al (J. Immunol., 122:2491 (1979)) using PEG as the initiator and HAT media (hypoxanthine $1 \times 10^{-4}$M, aminopterin $4 \times 10^{-7}$M, and thymidine $1.6 \times 10^{-5}$) as the selector of desired perpetuated clones. After suspension in HAT medium 0.1 ml aliquots were distributed into 96 well plates (Costar) at approximately $10^5$ cells/well. In Fusion #7, cells were plated into microtiter wells seeded with $2 \times 10^3$ murine macrophage per well, De St. Groth., S.F. et al, J. Immunol. Meth., 35:1 (1980). After two weeks, cultures were screened for cell growth and antibody production by the solid phase radioimmunoassay Solid Phase PVC Plate Radioimmunoassay: The solid phase radioimmunoassay was performed on flexible polyvinylchloride (PVC) microtiter plates (Cooke Laboratories) as described by Klinman et al, Ann. Immunol., 172C:489 (1976). The PVC plates were first coated with 25 µl of a crude preparation of MIS (approximately 1 mg/ml total protein), and incubated overnight at 4° C. Culture media from fusion cells were screened for anti-MIS antibody using affinity purified $^{125}$I-goat anti-mouse IgG1 antibody. Increasingly pure fractions of MIS (7,000- or 15,000-fold purification) were used to screen for anti-MIS antibody when mixed hybridomas were subcloned.

Radioimmunoassay Specificity Tests: In order to assess the specificity of monoclonal antibody for MIS, it was attempted to inhibit binding of anti-MIS antibody to MIS preparations by various proteins. Briefly, PVC plates were coated with 15,000-fold purified MIS. Then sample (culture media or IgG purified from ascites by DEAE chromatography) containing "anti-MIS" antibody was preincubated for 30 minutes with various other proteins including myoglobin, hemocyanin coupled to digoxin, insulin, and 1% horse serum. Samples were then applied to MIS coated PVC plates and the assay completed as described above.

Subcloning and Expansion of Hybridomas: Those hybridoma cell cultures identified as secreting antibody specific for MIS were subcloned by limiting dilution using Balb/C spleen cells as feeder layers. Colonies grown in wells seeded at 1 cell/well were considered monoclonal and tested for anti-MIS antibody by the radioimmunoassay. Positive clones were injected into pristane-primed Balb/C mice (0.5 ml pristane i.p., 1-2 weeks prior to cell injection) at a dose of $10^6$ cells/mouse. The resulting fluid was collected from each mouse and tested for the presence of anti-MIS antibody by other radioimmunoassay and the biological assay.

Biological Specificity Test: A summary of the protocol used is outlined in FIG. 2. The IgG fraction was isolated from approximately 10 ml of ascites fluid by DEAE chromatography in 0.02 M potassium phoshate buffer, pH 7, and coupled to a solid support, N-Hydroxysuccinimide activated Sepharose (HAS) as described by Gottlieb et al., J. Immunol., 114:51 (1975). Preparations containing MIS were then passed over columns of HAS-anti MIS IgG and eluted with PBS. Bound MIS was eluted from the column with 3M NH$_4$SCN (Mudgett, M., ibid, 120:293 (1978)), concentrated in an Amicon device and dialyzed against PBS. Crude MIS preparations, before and after passage through the HAS-anti-MIS IgG immunoadsorbent column (PBS eluted fraction) and the NH$_4$SCN eluted MIS were tested for biological activity in the organ culture assay system. As a control, the MIS preparation was also adsorbed to HAS coupled with mouse IgG isolated from ascites fluid which contained mouse antibodies to digoxin (Mudgett-Hunter, M. et al, Fed. Proc., 39:928 (1980)).

Determination of Immunoglobulin Isotype: Although culture media from fusion wells were screened in the solid phase PVC plate, RIA with $^{125}$I-goat anti-mouse IgG1, confirmation of the heavy chain isotype as IgG1 was carried out by the PVC plate RIA described above. In addition to the radiolabeled anti-IgG1 probe, anti-MIS antibody bound to the plate was reacted with radiolabeled goat anti-mouse isotypic antibodies (anti-IgG2a, anti-IgG2b, anti-IgG3, anti-IgA, and anti-IgM) purified from their respective antisera (Malloy, Springfield, Va.) by affinity chromatography. Myeloma proteins of a specific isotype (Litton Bionetics, Kensington, Md.) were coupled to cyanogen bromide activated Sepharose 4B (Cuatrecasas, P. et al, Biochem., 11:2291 (1972)) eluted with 3M NH$_4$SCN and extensively dialyzed against PBSA. Thirty $\mu$g of affinity purified antiisotope antibody was radiolabeled with 1 mCi of $^{125}$I by the Chloramine T method.

Results

Fusion Frequency: Significant titers of antibodies to Mullerian Inhibiting Substance (MIS) were obtained in serum from Balb/C mice immunized with the crude MIS preparation. By the solid phase PVC plate RIA significant antibody titer was detected in the mice immunized with MIS. Spleen cells from these mice were fused with the NS1 myeloma line. After two weeks in HAT media, wells were scored for cell growth in order to determine fusion frequency. As seen in Table I, both Fusion 5 and 7 gave fusion frequencies of 100%.

TABLE I

| | FUSION FREQUENCY | | |
|---|---|---|---|
| Fusion # | Fusion Frequency* | # Positive for MIS Antibody | % of Hybrids Positive for Antibody |
| 5 | 100% | 175 | 46 |
| 7 | 100% | 1 | 0.2 |

*In each fusion, culture media from 384 wells were assayed and cell growth was found to occur in all 384 wells.

Culture media from each well were preliminary screened for anti-crude MIS activity by RIA. For Fusion 5, 175 wells tested positive, giving an anti-MIS hybridoma frequency of 46%, while in Fusion 7, culture media from only one well contained antibody reactive to MIS, giving a hybridoma frequency of only 0.2% (Table I). In the case of Fusion 5, 28 of the hybridomas with the highest counts were chosen for further analysis, but after four weeks of growth in HT media, only five of the original "mixed" hybridomas still tested positive by the RIA. The RIA results for the five mixed hybridomas from Fusion 5 and the one from Fusion 7 are shown in Table II.

TABLE II

| RIA RESULTS FOR MIXED HYBRIDOMAS POSITIVE FOR CRUDE MULLERIAN INHIBITING SUBSTANCE* | | | | |
|---|---|---|---|---|
| | | Culture Media Counts/Minute | | |
| | | Days Post-Fusion | | Ascites |
| Fusion # | Hybridoma # | 19 | 49 | (1:10 Dil) |
| 5 | ID1 | 2412 | 1346 | n.d. |
| | IG10 | 2524 | 499 | 2643 |
| | IID5 | 1747 | 505 | 6858 |
| | IIH6 | 2461 | 730 | 6050 |
| | IVF4 | 2146 | 651 | 2734 |
| | Background** | 145 | 145 | 1008 |
| 7 | IVA6 | 4435 | 3691 | n.d. |
| | Background** | 169 | 715 | |

*The Mullerian Inhibiting Substance preparation used to coat the wells of the PVC plate for Fusion 5 represented a 200-fold purification of Mullerian Inhibiting Substance. For Fusion 7, this preparation was a 7,000-fold purification.
**Background counts determined from HT culture media and in the case of ascites, a 1/500 or 1/1,000 dilution of ascitic.

In order to augment anti-MIS antibody production, the five mixed hybridoma cell populations designated in Table I were injected into pristane primed mice for ascites fluid production. An IgG fraction was isolated from 10 ml of ascites by DEAE chromatography and coupled to HAS to produce HAS-anti-MIS immunoadsorbent columns.

By affinity chromatography, two (ID1 and IIH6) of the five potential anti-MIS mixed hybridomas from Fusion 5 were tested for their ability to adsorb MIS from a preparation representing a 200-fold purification of MIS. The fall through (PBS eluted) fraction was tested for the presence of biologically active MIS in the organ culture assay. As a positive control, the MIS preparation was also chromatographed on an affinity column prepared from ascites containing a hybridoma antibody (IgG) specific for another unrelated antigen (digoxin). Unadsorbed MIS preparation had 4+ Mullerian duct regression. The positive control (anti-digoxin antibody column) gave a diminished activity score of 3+, probably due to dilution, denaturation and/or losses as a result of the affinity chromatography manipulations. ID1 and IIH6 PBS wash had reduced biological activity of 0. The other three mixed hybridomas IG10, IID5, and IVF4 have not been tested but were preserved. The single mixed hybridoma from Fusion 7 was not subjected to this specificity test prior to subcloning because it was the only product obtained from this fusion.

Production of Monoclonal Lines for Mullerian Inhibiting Substance (MIS)

Mixed hybridomas ID1 and IIH6 were subcloned by limiting cell dilution on a feeder layer of nonimmune spleen cells. Only ID1 yielded clones which tested positive in the RIA. Of the 288 wells seeded at one cell/well, 28 showed cell growth, and seven of these 28 were positive for MIS by the criteria of the RIA. Ascites fluid was obtained for subclones IB2, IIG7, IIB6, and IIIB4. The single positive mixed hybridoma IVA6 from Fusion 7 was also subcloned. Of the 264 wells seeded at one cell per well, 12 were positive for crude Mullerian Inhibiting Substance. One IIIB3, was expanded in ascites fluid (see Table III).

TABLE III
RIA RESULTS FOR SUBCLONES POSITIVE FOR CRUDE MULLERIAN INHIBITING SUBSTANCE*

| Mixed Fusion | Hybridoma | Subclone | CM | Ascites (1:500 or 1:1000 Dil) Counts/Minute | Adsorbed Biological Activity |
|---|---|---|---|---|---|
| 5 | IK1 | IB2 | 4515 | 6167 | + |
|  |  | IIB6 | 5146 | 5663 | − |
|  |  | IIG7 | 2975 | 6459 | − |
|  |  | IIIB4 | 3271 | 4531 | − |
|  |  | BKg** | 211 | 346 |  |
| 7 | IVA6 | IIIB3 | 4783 | 5947 | + |
|  |  | BKg** | 715 | 760 |  |

*The Mullerian Inhibiting Substance preparations (Fraction Con-A II) used to coat the PVC plate for the two fusions represented a 7,000-fold purification.
**Same as for Table II.

Specificity of Monoclonal Lines for MIS—As Assessed by RIA

RIA titration curves of anti-MIS subclones IB2 and IIB6 are shown in FIG. 3 for both the culture media and ascites fluid obtained from these cell lines. Although the culture media from IB2 shows a slightly higher titer than IIB6, the titers of their respective ascites fluid are nearly identical. By the criteria of the RIA, both IB2 and IIB6 are specific for the Con A-2 MIS preparation used to coat the wells in the RIA. As indicated in Table III, however, only IB2 showed specificity for biologically active MIS.

As an indication of specificity for MIS, anti-MIS antibody binding to increasingly purer MIS preparations was tested. For example, binding of antibody IIIB3 present in culture media (CM) and in an IgG fraction prepared from ascites fluid by DEAE chromatography was tested on wells coated with two different MIS preparations (FIG. 4). The MIS preparations, Concanavalin A-fraction 2 and Matrex Gel Green A-fraction 2 (see Materials and Methods), represent 7,000-fold and a 15,000-fold increase in MIS purity respectively. As seen in FIG. 4, a greater amount of anti-MIS antibody bound to the Green-2 coated wells at each antibody dilution than to the Con A-2 coated wells. This increase in bound activity (cpm) is good indication for specificity to MIS since one would expect a higher density of MIS bound to the plate in the case of Green-2. Specificity of antibody IIIB3 for biologically active MIS was confirmed in the organ culture assay.

With the solid phase PVC-plate RIA, increased antibody binding to the wells on increased dilution was repeatedly seen for both ascites fluid and IgG preparations. The reason for this phenomenon is not entirely understood, but has been observed to occur with this RIA method for a variety of antigens used to coat the wells.

Specificity of Monoclonal Lines for MIS—As Assessed by Organ Culture Assay

As described before, an IgG fraction was obtained from each ascites fluid, coupled to HAS-Sepharose and the resulting affinity columns assessed for their ability to adsorb MIS activity. Monoclonal lines IB2 and IIIB3 successfully removed MIS from the preparation. Monoclonal lines IIB6, IIG7, and IIIB4, while significantly positive in the RIA (FIG. 3, Table III) did not remove MIS activity. Hybridomas IIB6, IIG7, and IIIB4 are thus considered to have a specificity for an antigen other than MIS present in the semipurified MIS preparation. Hybridoma IB2 and IIIB3, however, meets the criteria of specificity for MIS protein.

Recovery of MIS from Anti-MIS Affinity Column

Affinity columns prepared from both hybridomas IB2 and IIB6 and the control column were eluted with 3M $NH_4SCN$ in an attempt to recover adsorbed MIS activity. Following extensive dialysis against PBS, the $NH_4SCN$ fraction was analyzed for MIS activity in the organ culture assay. The results indicate that the $NH_4SCN$ fraction from IB2 contained biologically active MIS, while the same fraction from the control anti-digoxin column and IIB6 had no biological activity. These results confirm the specificity of hybridoma IB2 for MIS. The successful recovery of biologically active Mullerian Inhibiting Substance from an affinity column indicates the utility of this hybridoma in purification of MIS by affinity chromatography.

Cross-reactivity of Monoclonal Antibody to Other Proteins

In an attempt to assess the cross-reactivity of monoclonal antibody IIIB3 with other proteins, several were tested for their ability to inhibit the binding of IIIB3 to MIS-coated wells by the RIA described in Materials and Methods. Protein solutions of myoglobin, hemocyanin coupled to digoxin, insulin, 1% horse serum, were mixed with IIIB3 culture media and with a DEAE fraction prepared from IIIB3 ascites fluid. A fraction eluted from the Matrix Gel Green A column, but which did not contain biologically active MIS (Green-1), was similarly tested. As seen in FIG. 5, only the most concentrated solutions of myoglobin and hemocyanin coupled to digoxin inhibited the binding of IIIB3 to MIS to the extent of 25%. Further dilutions of all samples gave no significant inhibition. In contrast to these protein solutions, Green-2, a 15,000-fold purification of MIS, succeeded in giving 65–70% inhibition when tested at a total protein concentration of 0.11 μg/ml. Presumably, higher concentrations of Green-2 would successfully inhibit the binding of IIIB3 by 100%. Within the limited scope of proteins tested it thus appears that monoclonal antibody IIIB3 is specific for MIS. Monoclonal antibody IB2 was not tested for specificity in this system because on continued culturing, this cell line lost its ability to produce antibody. Line IIIB3 was deposited on Feb. 18, 1982 at the ATCC, has Accession Number HB 8114.

Discussion

Although an impure fraction of MIS was used to immunize Balb/C mice, somatic cell fusion of the immune spleen cells yielded two monoclonal hybridoma cell lines secreting antibody specific for MIS. Specificity of the antibody (IgG1) was demonstrated by its ability (1) to adsorb biologically active MIS prior to an organ culture assay and (2) to compete favorably with other potentially cross-reacting preparations in a solid-phase radioimmunoassay.

The reason why Fusion 7 gave such a low fusion frequency (0.2%, Table I) compared to Fusion 5 (46%, Table I) may be related to an increased purity of the immunizing MIS preparation. A more purified preparation of MIS may be less antigenic. It should be pointed out, however, that this fusion frequency represents only the frequency for antibodies of the IgG1 subclass, since for the sake of sensitivity, only $^{125}$I-anti-IgG1 was used as the probe in the PVC plate RIA. Consequently wells containing anti-crude MIS antibody of all other immunoglobulin classes were not detected.

Since MIS cannot as yet be obtained in an absolutely homogeneous form, demonstration of antibody specificity for MIS must rely on the antibody's ability to immunoadsorb biological activity prior to organ culture assay. Affinity columns prepared from mixed hybridoma ID1, and its subcloned line IB2, both adsorbed biological activity from a preparation of biologically active MIS. In the case of IB2, biological activity was recovered in a fraction subsequently eluted from the antibody affinity column with NH$_4$SCN. The slightly decreased level of MIS biological activity seen in the positive control (FIG. 3B) after the MIS preparation had passed through an affinity column prepared from a hybridoma specific for a different antigen (digoxin), probably reflects material losses due to handling and/or concomitant losses due to denaturation. The significance of this bioassay is that an affinity column prepared from hybridoma IB2 almost completely adsorbed biological activity, and this activity was recovered in an NH$_4$SCN fraction eluted from the same column. In contrast, no activity was recovered in the NH$_4$SCN fraction eluted from the control (antidigoxin) column.

Although the loss and recovery of biological activity of MIS upon adsorption and elution from an affinity column prepared with the presumed anti-MIS antibody is good evidence of antibody specificity for MIS, it does not eliminate the possibility that the hybridoma binds to a MIS carrier protein, for example. The existence of an MIS carrier protein, however, does not appear likely since it has been demonstrated in Swann, D. A. et al, Dev. Biol., 69:73 (1979), that a fraction with high biological activity for MIS can be extracted from whole testis using highly dissociative conditions followed by density gradient sedimentation. Since low molecular weight constituents tend to assume diffuse distribution in these gradients, the presence of MIS activity in a single high molecular weight protein fractions suggests that the activity is associated with a macromolecular constituent, a presumption that was confirmed by the finding that activity was retained by dialysis and after ultrafiltration. The highly dissociative conditions employed in the gradient and extraction procedures make unlikely the prospect that there exists a low molecular weight active moiety, and a high molecular weight carrier moiety, and that the monoclonal antibody is directed against this single macromolecular species.

The specificity of the organ culture assay is secure. Many false negatives can occur if the active MIS moiety is destroyed or diluted during purification or processing. Toxicity can cause a false positive reading which can, however, be avoided by comparing morphological changes around the retained Wolffian duct with those seen around the Mullerian duct. The loss of biological activity observed after passage through an "anti-MIS" affinity column is quite likely due to adsorption of the MIS molecule by an antibody specific for MIS rather than inactivation of the molecule, particularly since biological activity can subsequently be eluted by a chaotropic agent, NH$_4$SCN.

In an attempt to inhibit the biological activity of MIS, anti-MIS antibody was mixed with the MIS preparation and added to the media surrounding the tissue in the organ culture assay. In spite of repeated attempts, no direct inhibition of biological activity was observed. Since antibody did remove MIS from a crude MIS preparation, these results suggest that antibody binds MIS at determinants distant from the biologically active site of MIS but does not interfere with MIS activity.

Although IB2 subsequently lost its ability to specifically bind MIS, presumably due to lengthy time in culture and possible loss of its heavy or light chain genes due to hybridoma instability (Goding, J. W., J. Immunol. Meth., 39:285 (1980)), this unfortunate characteristic of the fused cells has been circumvented by immediate cloning and freezing once sufficient cells have been grown up, rather than waiting for biological assay confirmation as is required for this crude immunizing preparation. Another monoclonal antibody capable of absorbing MIS following the rapid "freeze-clone" method required to maintain stability in these hybridomas was rapidly achieved and allows the acquisition of the requisite library of monoclonal antibodies to MIS useful in the purification of MIS, in studies designed to determined tissue localization and distribution, assays, and the like.

Having now particularly described the invention, it will be appreciated that the same can be carried out by those skilled in the art within a wide range of immunogens, sensitizing procedures, concentrations, conditions, fusions, as well as determination and isolation of the antibodies and their use, without affecting the scope of the invention or any of the embodiments thereof.

What is claimed as new and intended to be covered by Letters Patent is:

1. In a method for preparing a hybridoma which secretes antibodies against an immunogenic material, comprising sensitizing an appropriate source with an immunizing amount of a preparation of said immunogenic material, obtaining from said source lymphocytes having immune activity against said immunogenic material, fusing said lymphocytes with an apropriate cell line to thereby form mixed hybridomas, and selecting said mixed hybridomas in the presence of said lymphocytes and said cell line, the improvement wherein:

said immunogenic material is present in said immunizing preparation in an amount not larger than 5% by weight, and wherein, after selection of said mixed hybridomas but prior to cloning, the method comprises the steps of:

raising ascites fluid with said mixed hybridomas, then detecting immune specificity against said immunogenic material in said ascites raised fluid; and thereafter cloning the ascites raised cells which show immune specificity againat said material.

2. The method of claim 1 wherein said immunogenic material is not independently available in substantially purified form.

3. The method of any of claims 1 or 2 wherein said immunogenic material is present in said preparation in less than 3% by weight.

4. The method of any of claims 1 or 2 wherein said immunogenic material is present in said preparation in less than 1% by weight.

5. The method of any of claims 1 or 2 wherein prior to raising ascites fluid with said mixed hybridomas, said mixed hybridomas are subjected to a preliminary screening to select mixed hybridomas having specificity towards said immunogenic material.

6. The method of any of claims 1 or 2 wherein said immunogenic material is selected from the group consisting of a protein, a nucleic acid, and a polysaccharide.

7. The method of any of claims 1 or 2 wherein said source is selected from the group consisting of an animal and a cell line.

8. The method of any of claims 1 or 2 wherein said preparation of said immunogenic material also comprises impurifying materials selected from the group consisting of proteins, nucleic acids and polysaccharides.

9. The method of any of claims 1 or 2, wherein said preparation of said immunogenic material is of biological origin.

10. A process of preparing monoclonal antibodies against an immunogenic material which comprises, preparing a hybridoma by the method of any of claims 1 or 2, and thereafter separating said monoclonal antibodies from said hybridoma.

11. The method of claim 1 wherein said immunogenic material is Mullerian Inhibiting Substance (MIS).

12. The method of claim 11 wherein said MIS is present in said preparation in less than 1% by weight.

13. The method of claim 11 wherein said MIS is at most 30-fold purified.

14. The method of claim 13 wherein said MIS is at most 7,000-fold purified.

15. The method of claim 11 wherein said source is a mouse.

16. The method of claim 11 wherein said appropriate cell line is P3-NS1-Ag4-1.

17. An in vitro composition consisting essentially of a continuous hybridoma cell line which secretes antibodies specific for MIS.

18. The composition of claim 17 wherein said cell line has ATCC deposit number HB 8114.

19. A process of preparing monoclonal antibodies against MIS which comprises preparing a hybridoma by the method of claim 11 and thereafter separating said monoclonal antibodies from said hybridoma.

20. In an immunoaffinity process for the purification of an immunogenic material present in a preparation, comprising sensitizing an appropriate source with an immunizing amount of said preparation, obtaining from said source lymphocytes having immune activity against said immunogenic material, fusing said lymphocytes with an appropriate cell line to thereby form mixed hybridomas, selecting said mixed hybridomas in the presence of said lymphocytes and said cell lines, cloning a desired hybridoma, separating monoclonal antibodies therefrom, and utilizing said monoclonal antibodies in said immunoaffinity chromatography, the improvement wherein:

said immunogenic material is present in said immunizing preparation in an amount not larger than 5% by weight, and wherein, after selecting of said mixed hybridomas but prior to cloning, the method comprises the steps of: raising ascites fluid with said mixed hybridomas, then detecting immune specificity against said immunogenic material in said ascites raised fluid; and thereafter cloning the ascites raised cells which show immune specificity against said material.

21. In an immunoaffinity process for the purification of MIS by using a solid phase-bound antibody, the improvement wherein said antibody is a monoclonal antibody against MIS.

* * * * *